(12) United States Patent
Wiklund

(10) Patent No.: US 6,197,006 B1
(45) Date of Patent: *Mar. 6, 2001

(54) SYRINGE HANDLE

(76) Inventor: Ernst Sigurd Gustaf Folke Wiklund, Lindevägen 40, Stockholm (SE), S-120 48

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/619,582

(22) PCT Filed: Oct. 10, 1994

(86) PCT No.: PCT/SE94/00951

§ 371 Date: Mar. 21, 1996

§ 102(e) Date: Mar. 21, 1996

(87) PCT Pub. No.: WO95/10313

PCT Pub. Date: Apr. 20, 1995

(30) Foreign Application Priority Data

Oct. 11, 1993 (SE) .................................................. 93003325

(51) Int. Cl.[7] .................................................. A61M 5/00
(52) U.S. Cl. .................................................. 604/263
(58) Field of Search .................................. 604/116, 117, 604/164, 165, 166, 263, 174, 177, 178, 171, 192, 115, 198; 128/DIG. 26; 606/108

(56) References Cited

U.S. PATENT DOCUMENTS

| D. 208,611 | * | 9/1967 | Smith, Jr. | 604/177 |
|---|---|---|---|---|
| 3,782,383 | * | 1/1974 | Thompson et al. | 604/177 |
| 4,596,553 | * | 6/1986 | Lee | 604/117 |
| 4,662,870 | * | 5/1987 | Augustine et al. | 604/117 |
| 4,735,615 | * | 4/1988 | Uddo, Jr. et al. | 128/DIG. 26 |
| 5,176,655 | * | 1/1993 | McCormick et al. | 604/198 |
| 5,217,438 | * | 6/1993 | Davis et al. | 604/198 |
| 5,403,283 | * | 4/1995 | Luther | 604/164 |
| 5,433,703 | * | 7/1995 | Utterberg et al. | 604/177 |

FOREIGN PATENT DOCUMENTS

| 2 306 068 | 8/1973 | (DE) . |
|---|---|---|
| 42 44 653 A1 | 9/1993 | (DE) . |
| A1 4244 653 | 9/1993 | (DE) . |
| 1 416 432 | 12/1975 | (GB) . |

* cited by examiner

Primary Examiner—Sharon Kennedy
Assistant Examiner—Ann Yen Lam
(74) Attorney, Agent, or Firm—Pennie & Edmonds LLP.

(57) ABSTRACT

Ergonomic handle for a syringe intended for puncturing blood vessel walls and establishing blood path connections. The typical syringe comprises a tube body and a needle body. The handle prevents unintended displacements between the tube body and the needle body and permits placement of the thumb and forefinger at the side and the tip of the puncture needle for more precision in use.

12 Claims, 3 Drawing Sheets

A - A

B - B

C - C

D - D

E - E

F - F

G - G

H - H

J - J

SYRINGE HANDLE

TECHNICAL FIELD

The invention relates to an ergonomically designed handle for a syringe that includes a tubular body and a needle body which is used to puncture blood vessels and establish blood path connections.

BACKGROUND ART

In the medical field, it is frequently required to establish a connection between blood vessels (veins and arteries) and injectors or containers of different kinds. The connection must be made with total sterility. Leakage must be avoided as far as possible. Examples of treatments requiring blood vessel contact are blood transfusion inclusive blood giving, blood sampling with the assistance of test containers under negative pressure, and intravenous supply of medicine, nourishment or just liquid for blood volume expansion, commonly called a drip. In all these applications it is essential that the puncture of the vessel wall can be done without damage to the surrounding tissues. Failures are unpleasant, even under the best circumstances, but may cause serious damage as well.

A common syringe for insertion in blood vessels of different kinds is shown in FIG. 1. The syringe consists of a tube body (1) with a channel that continues in a thin plastic tube (3). The rear opening of the tube body is designed with a conical widening for attachment to a syringe or a catheter. The opening is at the beginning filled by the hollow needle (4), which continues with the needle body (5), the rear part of which has a transparent room, which gets filled with blood, when satisfactory blood vessel contact has been established. Through the channel runs the hollow puncture needle (4) with a beveled, sharpened tip, which extends a few millimeters in front of the front end of the thin plastic tube.

When establishing a blood vessel connection, one chooses a suitable, superficial blood vessel (vein or artery, depending upon type of treatment) and tries to direct the tip of the puncture needle to penetrate the skin just over the chosen blood vessel so that the tip hits the vessel centrally. After penetration of the vessel wall the puncture needle with the plastic tube can be directed axially obliquely into the blood path. When the above mentioned transparent room behind the needle starts filling with blood the needle body with the belonging puncture needle is kept still, while the tube is advanced so that the needle tip no longer is in front of the end of the plastic tube. This is done to prevent the needle tip from hurting the vessel wall, when the plastic tube afterwards is brought forward into the blood path, to the main part of its length, with the aid of the tube body. When the plastic tube has reached the desired position in the blood path, the tube body is kept still. The puncture needle, which, so far, has prevented leakage by its close fit to the inner wall of the plastic tube, is withdrawn with the needle body and the desired connection to the syringe, container or catheter is made.

For reasons of sterility the plastic tube must not be touched before or during the insertion into the blood lumen. The distance from the needle tip to the grip around the needle body is long. The grip surfaces are not well defined, especially as the hands most frequently have to be provided with gloves. The insertion demands a number of complicated changes of direction. After the skin penetration there is no visible indication of the position of the needle tip. Moreover, the blood vessels are frequently badly fixed under the skin and have troublesome tendencies to "roll away".

In spite of these, from the ergonomic point of view, very unfavorable circumstances, experienced nurses with daily training become very skilled and seldom fail. The circumstances are different for doctors, nurses, ambulance crews and apprentices, who are infrequently put to the task. Failures will cause the patient discomfort and are embarrassing to the operator. Further, loss of valuable material will arise.

Amendment proposals concerning the ergonomics at the establishment of vein and artery connections and similar operations can be found in the German "Offenlegungsschriften" 2306068 and 4244563. The solution of the problem according to the former is applicable to injection needles without a surrounding plastic tube only. While it is true that the latter reference mentions the possibility of combination with a plastic tube, the proposed design causes large risks of damages as no firm connection between the needle body and the tube body exists. As will be explained below unintended displacements between those parts cause serious moments of risk.

SUMMARY OF THE INVENTION

The invention concerns a handle (6) for a syringe, the syringe comprising a needle body (5) with a hollow needle (4) of suitable material and a tube body (1) with a thin plastic tube (3) intended for the puncture of blood vessel walls and the establishment of blood path contact. The handle is designed to admit placement of the thumb and the forefinger at the side of the tip of the needle (4) and in its proximity and prevents unintended displacements between the needle body (5) and the tube body (1) during the puncture phase.

In a preferred embodiment of the invention, the grip part (7) of the handle is designed so other parts of the hand can help the governing of the syringe. Examples of such embodiments of the invention are shown in FIGS. 2 and 3.

Further, the handle (6) should be designed to permit one to easily disengage the tube body, without an essential change of position of the thumb/forefinger grip and without influencing the stable fixation to the needle body. When the tube body has been disengaged, it may by the other hand of the operator be advanced into the lumen to a suitable position without changing the position of the needle body and with it the puncture needle position. The handle may be provided with an indication stick (8) that shows the position of the tip of the puncture needle and may be of good assistance to operators without daily training.

When the tube body (3) has been advanced to the desired position, the puncture needle (4) is removed. To prevent blood flow through the tube body's rear end, which until now has been made tight by the needle body, the operator begins the removal by compressing the skin area above the front end of the plastic tube with his or her other hand. This is done until he or she has withdrawn the puncture needle, let go the handle with the puncture needle and placed the stopper, intended for this purpose, in the rear end of the tube body. Now the operator has both hands free and can fix and flow-test the tube body and separate the needle body (5) from the handle, which may be taken care of for cleaning, autoclaving and repackaging.

The handle grip (7) must, besides being ergonomically pleasant, provide a comfortable but firm and stable fixation to the needle body (5), suitably to the shield (9), and to the tube body (1), suitably to one of its wings (2). In this way a sure protection against unintended displacement of the needle tip in relation to the tube end is obtained. The needle tip is very sharp. Undesired displacements of their mutual position may cause the sharpened edges to cut loose plastic fragments from the tube tip. The fragments may get into the blood path. This may have incalculable consequences.

When the handle grip has been mounted, the operator may begin a skin and vessel puncture after the usual hygienic preparations. As shown in FIG. 4, the thumb/forefinger grip near the needle tip is ergonomically favorable and permits use of the fine motor movements of the hand. The bigger muscle groups in forearm, upper arm and trunk need normally not take part. The person who so wishes may get guidance at and after the vessel wall penetration by the indication stick (8), which may be provided on the handle.

A handle with the qualities mentioned above may be designed in several different ways. A couple of those different embodiments are shown in FIGS. 2 and 3.

DETAILED DESCRIPTION OF THE PREFERRED EMBODIMENTS

Figure 1A:
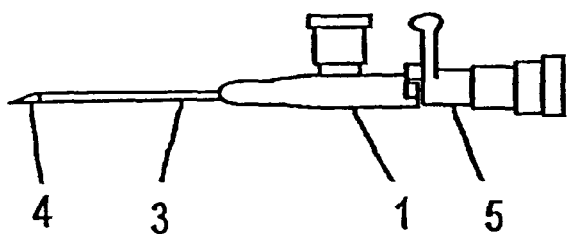
FIGS. 1A–B shows two parallel projections, in two perpendicular planes of a so-called VENFLON®-syringe, which is suitable for use with the handle of the invention. VENFLON is a registered trade mark.
Figure 1B:
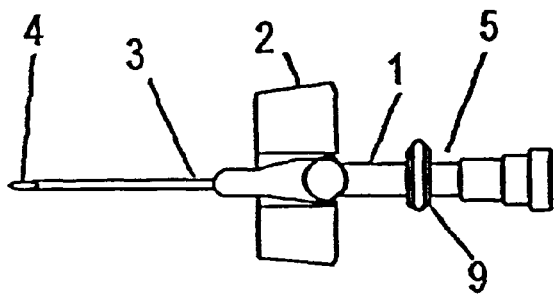
Figure 2A:
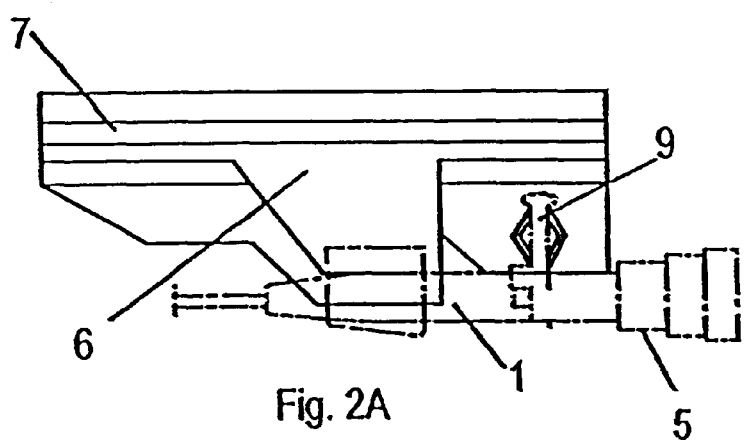
FIGS. 2A–C shows an embodiment for carrying out the invention.
Figure 2B:
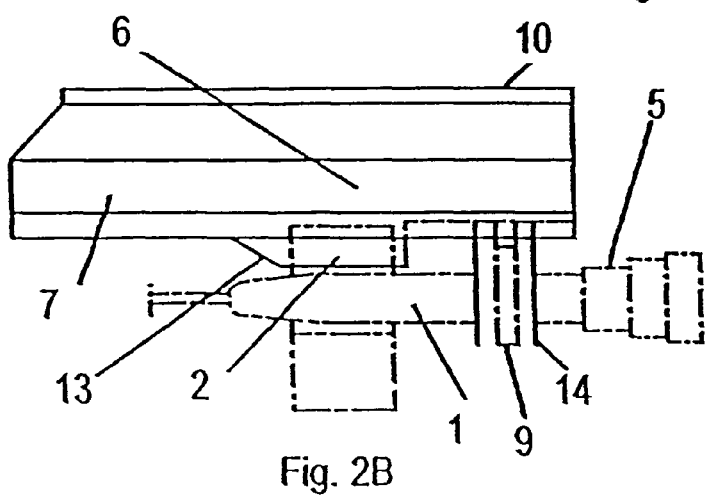
Figure 2C:
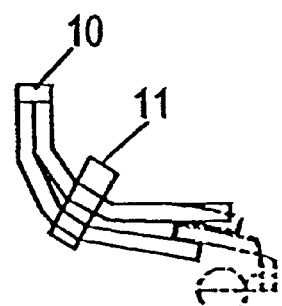
Figure 3A:
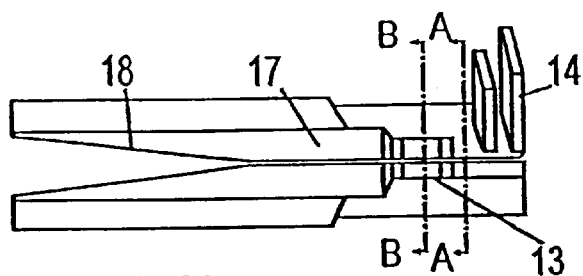
FIGS. 3A–N shows another embodiment for carrying out the invention.
Figure 3B:
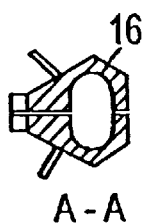
Figure 3C:
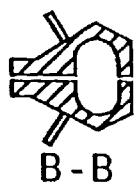
Figure 3D:
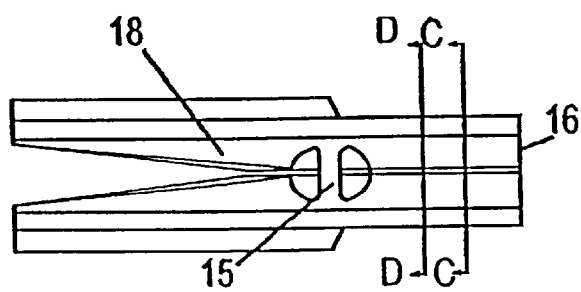
Figure 3E:
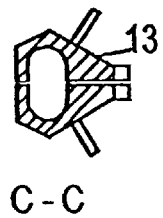
Figure 3F:
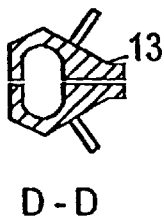
Figure 3G:
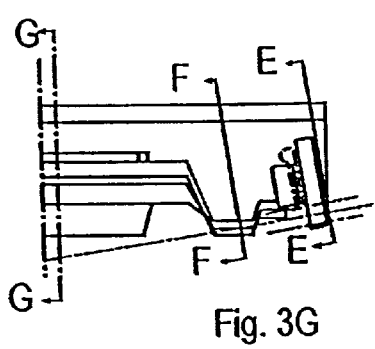
Figure 3H:
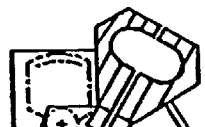
Figure 3I:
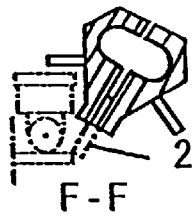
Figure 3J:
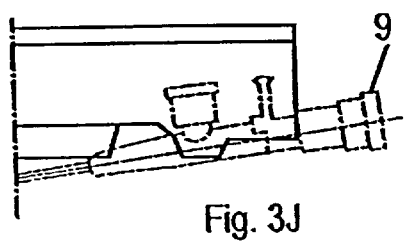
Figure 3K:
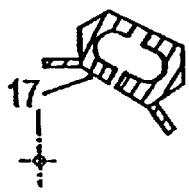
Figure 3L:
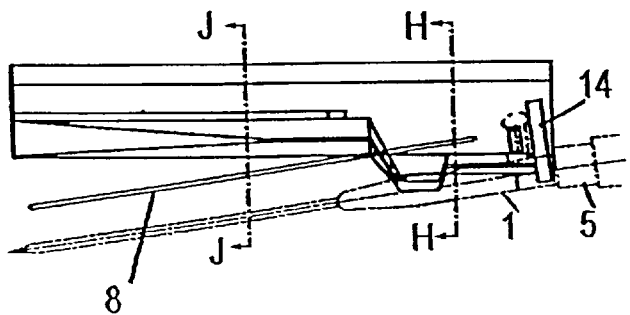
Figure 3M:
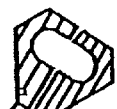
Figure 3N:
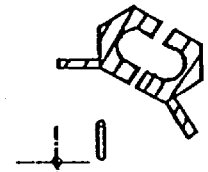
Figure 4:
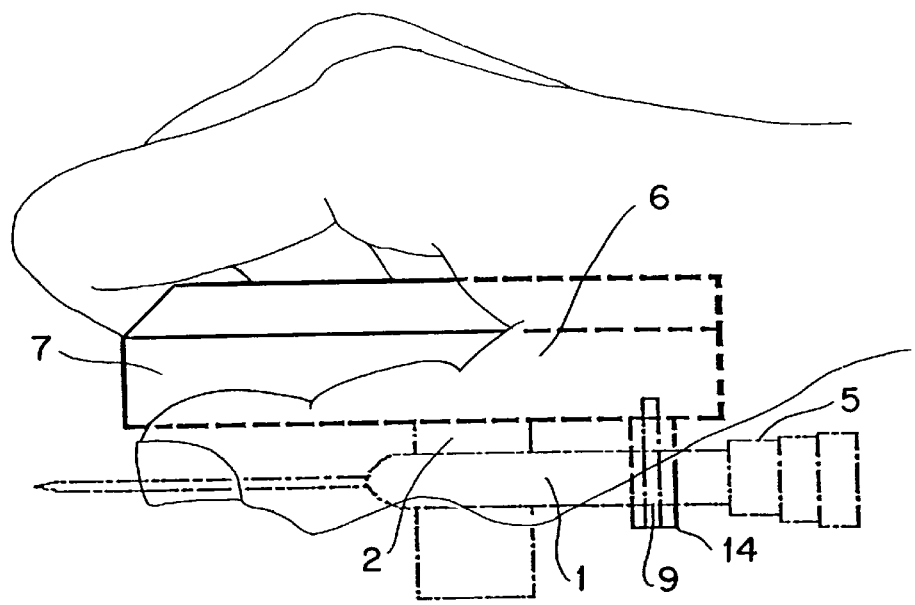
FIG. 4 shows use of the handle with a syringe by an operator.
Figure 5A:
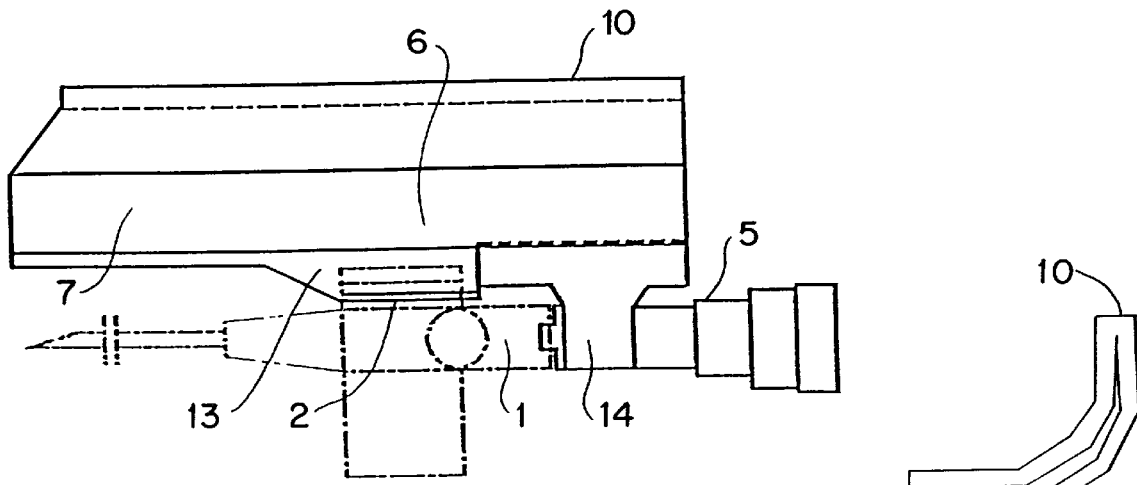
FIGS. 5A–B shows the handle attached to a syringe that does not have a shield.
Figure 5B:
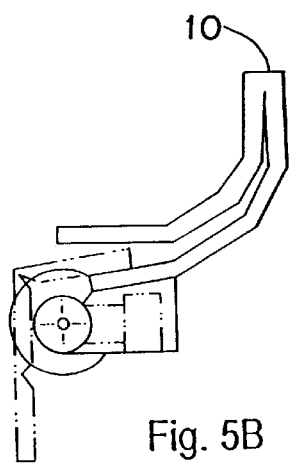

FIG. 2 shows a handle (6) comprising two straight beams both with an almost uniformly curved section and joined by a border (10), of a suitable polymer material with springy hinge function, and provided with a snap lock (11) at the back end. The beams are designed to enclose one wing of the tube body (2) and fix it with the aid of the snap lock (11). One of the beams, preferably the one below, is provided with a projecting squeeze arrangement (14) suitable to be placed over the shield (9) of the needle body (5) from the side or from above, at which the rear half of the squeeze arrangement (14) first meets the back surface of the shield (9) to prevent tendencies for backward movement of the needle body (5). In the squeezed position the shield (9) becomes fixed not just in height and side position but also in a defined direction essentially parallel to the squeeze arrangement (14). With the preserved thumb/forefinger grip the snap lock (11) shall allow opening with the little or ring finger, at which the tube body's wing (2) is let free and the tube body (2) may be advanced, while the needle body (5) still may be controlled and manipulated by the preserved thumb/forefinger grip. As shown in FIG. 5, the handle is attachable to a syringe that does not have a shield. The squeeze arrangement 14 contacts the tube body where the shield would be located.

FIG. 3 shows a handle constructed as a hollow hexagonal rod with a function similar to a clothes-pin. The hexagonal rod is, except the piece (15) of the back wall (16) which serves as a springy hinge, cut longitudinally through the front wall (17) and the mentioned back wall (16). The front part of the rod is cut obliquely to form shanks (18) of the clothes-pin. The shank angles may preferably be larger at the front (17) to give a bit larger opening of the rear front wall cut of the rod. The rear part of the front wall (17) of the rod has a pair of projecting jaws (13) preferably provided with one or more teeth intended to fix one wing of the tube body firmly. At an upper wall, the rear part of the rod has a squeeze arrangement (14) suitable for the shield (9) of the needle body (5). This is in relation to the longitudinal cut. The rear half of this squeeze arrangement (14) is made to contact the rear wall of the shield (9) to prevent the tendency of the needle body (5) to move backwards in relation to the tube body (1). The squeeze arrangement (14) is designed to give a firm fixation of the shield (9) in the desired needle direction and height and side.

The design provides that one, with an unchanged thumb/forefinger grip, first can securely direct the skin and blood vessel puncture and after that can open the clothes-pin to let the tube body wing (2) free. They may then with ease advance the tube body (2), while the needle body (5) is still fixed in the handle in an unchanged position, until the needle body (5) can finally be withdrawn and the rear end of the tube body (1) made tight by the stopper that until now has been sitting at the rear end of the needle body.

The figure shows the possibility of attaching the earlier mentioned indicating stick (8) to show the position of the needle tip and profiles with the object first to prevent the gloves of the operator from contaminating the plastic tube or the needle tip and second to reinforce the shanks of the clothes-pin. In the example, a hexagonal rod has been chosen and this is, from the grip point of view, the preferred design. However, other polygonal and circular crosscuts are just as useful even if less grip-friendly.

A handle according to the invention may be designed as a single-use item. Then nothing prevents designing the handle as permanently bound to the needle body (5) and temporarily bound to and easily disengaged from the tube body (1). As the invention primarily is intended as expedient to operators that due to deficient training otherwise may have difficulties performing blood vessel punctures in the correct way, designing as a separate attachment and article for repeated use is preferred.

As shown in FIG. 3, attaching the handle for repeated use to a syringe is done as follows: The rear half of the squeeze arrangement (14) is brought into contact with the back side of the shield (9) and to prevent backward movements of the puncture needle (4) in relation to the plastic tube (3). After that, the jaws (13), intended to enclose one wing (2) of the tube body, are opened by pressing together the shanks (18). The wing is brought into the gap between the jaws (13) and fixed there by letting go of the pressure on the shanks (18). During the entire procedure the rear half of the squeeze arrangement (14) rests against the back side of the shield (9). After the fixation of the tube body's wing (2), the handle is turned around an axis, which is roughly parallel to the axis of the syringe and runs through the joint of the wing (2), until one reaches the desired grip position while the squeeze arrangement (14) is brought to its final position at the needle body (5) and fixed there. Mounting the handle as shown in FIG. 2 and variants of the exemplified handles are done in the same way as far as applicable.

What is claimed is:

1. A method of mounting a releasable handle to a syringe, the method comprising the steps of:

providing a syringe including a needle body with a puncture needle and having a shield connected to the needle body, and a tube body with a tube that surrounds the puncture needle, and a wing connected to the tube body;

providing a handle having a squeeze arrangement and a pair of jaws;

bringing and maintaining the squeeze arrangement in contact with the shield to engage the shield with the squeeze arrangement;

clamping the wing of the tube body between the jaws;

rotating the handle around an axis roughly parallel to an axis of the syringe until a desired grip position is reached; and affixing the squeeze arrangement to the shield of the needle body.

2. A handle for a syringe that includes a first body with a puncture needle having a tip, a second body with a tube that surrounds the puncture needle and enters a blood vessel together with the needle and remains in the vessel when the needle is withdrawn, the handle comprising:

a grip arrangement that invites thumb/forefinger placement thereon aligned with and adjacent to the tip of the puncture needle of the syringe;

a first connection extending from the grip arrangement for connecting to the first body of the syringe; and a second connection extending from the grip arrangement for connecting to the second body of the syringe, that can be disengaged during the use of the syringe when the needle tip penetrates the blood vessel wall, with minimal disturbance of the position of the needle tip.

3. A handle and syringe combination, the syringe including a first body with a puncture needle having a tip, and a second body with a tube that surrounds the puncture needle and enters a blood vessel together with the needle and remains in the vessel when the needle is withdrawn, and the handle comprising:

a grip arrangement that invites thumb/forefinger placement thereon aligned with the needle of the syringe;

a first connection extending from the grip arrangement for connecting to the first body of the syringe having the needle with the tip; and a second connection extending from the grip arrangement for connecting to the second body of the syringe having the tube that surrounds the needle, the second body being disengageable from the first body during the use of the syringe when the needle tip penetrates the blood vessel wall with minimal disturbance of the position of the needle tip;

wherein the tube enters a blood vessel together with the needle and remains in the vessel when the needle is withdrawn, and wherein the first connection is fixed to the first body of the syringe and the second connection is releasably fixed to the second body of the syringe.

4. The combination of claim 3 wherein the first body further comprises a shield attached to the first connection of the grip arrangement.

5. The combination of claim 3 wherein the second body further comprises a wing attached to the second connection of the grip arrangement.

6. A handle for a syringe that includes a needle body with a puncture needle having a tip, a tube body with a tube that surrounds the puncture needle, and a wing fixed to and extending from the tube body, the handle comprising:

a rod that invites thumb/forefinger placement thereon;

a projecting jaw extending from the rod and capable of being releasably fixed to the wing of the tube body such that the wing is easily releasable during use of the syringe when the needle tip and tube penetrate a blood vessel wall, with minimal disturbance of the position of the needle tip; and a squeeze arrangement extending from the rod and capable of being fixed to the needle body.

7. The handle of claim 6 wherein the rod further comprises:

two roughly parallel shanks that are hingedly connected and positioned adjacent the rod; and two halves of the projecting jaw, each half extending from each shank so that pressure may be applied to a first end of the shanks to form a space between the second end of the shanks and the projecting jaw halves so that the wing of the tube body is capable of being placed within the space between the projecting jaw halves and fixed between the projecting jaw halves by releasing the pressure applied to the shanks.

8. The handle of claim 6 wherein the handle further comprises an indicating stick attached to the rod that shows the position of the tip of the needle.

9. The handle of claim 6 further comprising:

a syringe including, a needle body having a puncture needle with a tip; and a tube body having a tube that surrounds the puncture needle, and a wing fixed to and extending from the tube body;

wherein the projecting jaw is fixed to the wing of the tube body and the squeeze arrangement is fixed to the needle body.

10. The handle of claim 9 further comprising:

a shield attached to the needle body;

wherein one shank includes the squeeze arrangement that is capable of being fixed to the shield of the needle body.

11. The handle of claim 9 wherein the squeeze arrangement is permanently fixed to the needle body.

12. A method of mounting a releasable handle to a syringe, the method comprising the steps of:

providing a syringe including a needle body with a puncture needle, and a tube body with a tube that surrounds the puncture needle, and a wing connected to the tube body;

providing a handle having a squeeze arrangement and a pair of jaws;

bringing and maintaining the squeeze arrangement in contact with the needle body to engage the needle body with the squeeze arrangement;

clamping the wing of the tube body between the jaws;

rotating the handle around an axis roughly parallel to an axis of the syringe until a desired grip position is reached; and affixing the squeeze arrangement to the needle body.

* * * * *

UNITED STATES PATENT AND TRADEMARK OFFICE
CERTIFICATE OF CORRECTION

PATENT NO. : 6,197,006 B1  
DATED : March 6, 2001  
INVENTOR(S) : Ernst Sigurd Gustaf Folke Wiklund It is certified that error appears in the above-identified patent and that said Letters Patent is hereby corrected as shown below:

Claim 10,  
Between lines 1 and 2 insert -- a needle body; and --.

Claim 11,  
Lines 1 and 2, change "squeeze arrangement is permanently fixed to the needle body" with -- first connection is fixedly secured to the first body of the syringe --.

Signed and Sealed this

Eighteenth Day of December, 2001

Attest:

JAMES E. ROGAN  
*Attesting Officer*  *Director of the United States Patent and Trademark Office*